(12) United States Patent
Chen et al.

(10) Patent No.: US 8,518,461 B2
(45) Date of Patent: Aug. 27, 2013

(54) USE OF BAMBOO VINEGAR FOR TREATING INFLAMMATION

(75) Inventors: Ann Chen, Taipei (TW); Kuo-Feng Hua, I-Lan (TW); Shuk-Man Ka, Taipei (TW); Jia-Ming Chang, Taipei County (TW); Yung-Jen Tsai, Taipei County (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 13/448,722

(22) Filed: Apr. 17, 2012

(65) Prior Publication Data

US 2013/0171275 A1    Jul. 4, 2013

Related U.S. Application Data

(60) Provisional application No. 61/581,261, filed on Dec. 29, 2011.

(51) Int. Cl.
*A01N 65/00* (2009.01)

(52) U.S. Cl.
USPC ............................................................ 424/725

(58) Field of Classification Search
None
See application file for complete search history.

(56) References Cited

FOREIGN PATENT DOCUMENTS

JP          411060465 A    *   3/1999

* cited by examiner

*Primary Examiner* — Michael Meller
(74) *Attorney, Agent, or Firm* — WPAT, P.C.; Anthony King (57) ABSTRACT

The present invention relates to a method for treating inflammation comprising administering a subject in need thereof with a therapeutically effective amount of a composition comprising bamboo vinegar or the phenolic fraction thereof. The method for preparing the phenolic fraction is also provided.

4 Claims, 14 Drawing Sheets

USE OF BAMBOO VINEGAR FOR TREATING INFLAMMATION

FIELD OF THE INVENTION

The present invention relates to a new use of bamboo vinegar for treatment of inflammation related diseases.

BACKGROUND OF THE INVENTION

Bamboo charcoal, commonly used as a fuel component, a deodorizer, or an absorbent, is produced by heating bamboo at very high temperature in an airless vessel. Bamboo vinegar is a natural liquid derived from the condensed vapor procured in bamboo charcoal production. Bamboo vinegar is composed of 80%~90% water, high acetic acid, tar and many other organic constituents and has sour and smoky odors and with PH of 2.5 to 2.8 (Akakabe Y, Tamura Y, Iwamoto S, Takabayashi M, Nyuugaku T. Volatile organic compounds with characteristic odor in bamboo vinegar. Biosci Biotechnol Biochem. 2006 November; 70(11):2797-9). It has been widely added to soap or toothpaste used as an anti-bacterial, anti-fungal and deodorant agent. It is also applied in cosmetics and horticultural products. Composting is an effective methodology for the treatment of organic waste; however, the disadvantages of composting are the nitrogen loss through ammonia volatilization and the presence of heavy metals. Addition of bamboo vinegar to pig manure composting is able reduce nitrogen loss and immobilize Cu and Zn (Chen Y X, Huang X D, Han Z Y, Huang X, Hu B, Shi D Z, Wu W X. Effects of bamboo charcoal and bamboo vinegar on nitrogen conservation and heavy metals immobility during pig manure composting. Chemosphere. 2010; 78(9): 1177-81).

Bamboo vinegar is recognized to show herbal properties including the ability to assist in the discharge of unnecessary waste matters and toxins from the human bodies. In Japan, bamboo vinegar even has become health food drinks. Since bamboo vinegar is produced along with bamboo charcoal production, the safety and possible carcinogenicity of bamboo vinegar should be concerned if bamboo vinegar is applied in human. The carcinogenic and tumor-promoting potential of bamboo vinegar has been determined by the in vitro BALB/c 3T3 A31-1-1 cell transformation assay system and found that bamboo vinegar did not act as a tumor promoter after being diluted more than $10^4$-fold with water (Y. Kimura, S. Suto, and M. Tatsuka, "Evaluation of Carcinogenic/Co-carcinogenic Activity of Chikusaku-eki, a Bamboo Charcoal By-product Used as a Folk Remedy, in BALB/c 3T3 Cells", Biol. Pharm. Bull., 25:1026-1029, 2002).

Recently bamboo vinegar has drawn the attention of medical researches for the treatment of dermatitis, diabetes and other human maladies. However, none of the prior art references disclosed the use of distillong product of bamboo vinegar in inflammatory disorder.

BRIEF SUMMARY OF THE INVENTION

It is unexpectedly found in the present invention that bamboo vinegar has a new use in treatment for inflammation. Therefore, the present invention provides a new approach for treatment of inflammation with bamboo vinegar.

In one aspect, the invention provides a method for treatment of inflammation comprising administering a subject in need thereof a therapeutically effective amount of a composition of bamboo vinegar.

In another aspect, the invention provides a method for preparing a phenolic faction of bamboo vinegar having anti-inflammatory activity comprising the steps of: (a) distilling bamboo to obtain a distilled product; (b) extracting the distilling product by a first aqueous alkaline solution to collect an first organic layer; (c) extracting the first organic layer by a second aqueous alkaline solution to collect an aqueous layer; and (d) extracting the aqueous layer by an ether-type solvent and an aqueous acidic solution to collect a second organic layer.

BRIEF DESCRIPTION OF THE DRAWINGS

For the purpose of illustrating the invention, there are shown in the drawings embodiments. It should be understood, however, that the invention is not limited to the preferred embodiments shown. In the drawings.

DETAILED DESCRIPTION OF THE INVENTION

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

The table below shows the abbreviations for some terminologies.

| Abbreviation | Terminology |
| --- | --- |
| BV | bamboo vinegar |
| iNOS | inducible nitric oxide synthase |
| NO | nitric oxide |
| IL-6 | interleukin-6 |
| TNF-α | tumor necrosis factor-α |
| COX-2 | cyclooxygenase-2 |
| LPS | lipopolysaccharide |
| PKC | protein kinase C |
| NF-κB | nuclear factor-kappa B |
| GC | gas chromatography |
| FID | flame ionization detection |
| ELISA | enzyme-linked immunosorbent assay |
| MAPK | mitogen-activated protein kinase |

As used herein, the term "bamboo vinegar" refers to a natural liquid derived from the condensed vapor procured in bamboo charcoal production. Bamboo vinegar is known to be composed of 80%~90% water, high acetic acid, tar and many other organic constituents, which has sour and smoky odors and a PH of 2.5 to 2.8

In the present invention, it is unexpectedly found that bamboo vinegar has anti-inflammatory activity, in terms of the effects in inhibiting the expression of NO in LPS-activated macrophages, in reducing the expression of LPS-induced iNOS, NO, and IL-6, but does not inhibit the expression of TNF-α and COX-2 in LPS-activated macrophages (as shown in FIGS. 2A to 2D). As shown in FIGS. 3A to 4B, bamboo vinegar inhibited PKC-α and PKC-δ signaling pathway in LPS-activated macrophages, but does not affect MAPK, AKT and NF-κB. It is also found that the phenolic fraction of bamboo vinegar inhibits NO expression in LPS-activated macrophages (see FIGS. 5A and 5B). Therefore, the invention provides a method for treatment of inflammation comprising administering a subject in need thereof a therapeutically effective amount of a composition comprising bamboo vinegar.

According to the invention, bamboo vinegar may be obtained by any commonly used, or known standard method for bamboo charcoal production. For example, the bamboo vinegar may be obtained by distilling bamboo at a distillation temperature of 90° C.~150° C., such as about 145° C.~150° C. In addition, the distilled product may be further extracted by an organic agent, such as a ether-type solvent. In the invention, one example of the ether-type solvent is diethyl ether. In one particular example of the invention, the bamboo vinegar is obtained by distilling bamboo vinegar and further extracting with diethyl ether.

The invention also provides a method for preparing a phenolic faction of bamboo vinegar having anti-inflammatory activity comprises the steps of: (a) distilling bamboo to obtain a distilled product; (b) extracting the distilling product by a first aqueous alkaline solution to collect a first organic layer; (c) extracting the first organic layer by a second aqueous alkaline solution to collect an aqueous layer; and (d) extracting the aqueous layer by a ether-type solvent and an aqueous acidic solution to collect a second organic layer. According to the invention, the pH valve of the first aqueous alkaline solution ranges from 7 to 8; the pH value of the second aqueous alkaline solution ranges from 11 to 13; and the pH value of the aqueous acidic solution ranges from 2 to 4. In one example of the invention, the first aqueous alkaline solution comprises a solution of $NaHCO_3$, preferably at a pH value ranging from 7 to 8; the second aqueous alkaline solution comprises a solution of NaOH preferably at a pH value ranging from 11 to 13; the aqueous acidic solution comprises a solution of $H_2SO_4$ or HCl preferably at a pH value ranging from 2 to 4; and the ether-type solvent is diethyl ether.

In addition, the invention provides a pharmaceutical composition for treatment of inflammation comprises a therapeutically effective amount of the composition of bamboo vinegar or the phenolic faction thereof together with one or more pharmaceutically acceptable carriers, diluents or excipients.

The term "therapeutically effective amount" as used herein refers to an amount of a pharmaceutical agent which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

The term as used herein "pharmaceutically acceptable carrier, diluent or excipient" refers to a carrier(s), diluent(s) or excipient(s) in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation.

According to the present invention, the pharmaceutical composition may be adapted for administration by any appropriate route, including but not limited to oral, rectal, nasal, topical, vaginal, or parenteral route. In one particular example of the invention, the pharmaceutical composition is formulated for oral administration. Such formulations may be prepared by any method known in the art of pharmacy.

The present invention is further illustrated by the following examples, which are provided for the purpose of demonstration rather than limitation.

EXAMPLE

Materials

LPS (from *Escherichia coli* 0111:B4), anti-phospho-ERK1/2, anti-phospho-JNK1/2, anti-phospho-p38 and anti-actin antibodies were purchased from Sigma (St. Louis, Mo.). Anti-ERK1/2, anti-JNK1/2, anti-p38, anti-phospho-PKC-α, anti-phospho-PKC-δ, anti-PKC-α/β/γ, anti-iNOS, anti-COX-2, anti-IL-1β and anti-caspase-1 antibodies were obtained from Santa Cruz Biotechnology (Santa Cruz, Calif.). TNF-α, IL-6, and IL-1β ELISA kits were purchased from R&D Systems (Minneapolis, Minn.). AlamarBlue® assay kit was purchased from AbD Serotec Ltd (Oxford, UK). QUANTI-Blue™ reagent was purchased from InvivoGen (San Diego, Calif.).

Bamboo

Moso bamboo (Phyllostachys heterocycla Milf) was provided by Pu Yuan Co. Ltd., Nantou, Taiwan. The specimens of a size of 25 mm×25 mm×3 mm (Length×Weight×Thickness) were prepared. All specimens were conditioned to equilibrium at 20° C. with 65% relative humidity (RH) for about four weeks. Then, the average moisture content and density were measured.

Bamboo Vinegar

These bamboo vinegars, collected at different temperatures during the manufacturing process of charcoal from moso bamboo, were provided by the Division of Forest Utilization, TFRI Taipei, Taiwan. These bamboo vinegars were collected at temperatures ranging from 90° C. to 150° C. based on the temperature measured by a thermocouple at the exit of a smoke funnel of a furnace during the bamboo charcoal manufacturing process (pyrolysis). The different groups of bamboo vinegar were collected at 90-92° C. (BV-1), 99-102° C. (BV-2), 120-123° C. (BV-3) and 145-150° C. (BV-4), respectively.

Treatment of Material

Bamboo vinegar collected at 145-150° C. (BV-4) was extracted with ether to obtain the ether-extracted product, which was then further separated into acidic, neutral, and phenolic fractions.

Cell Cultures

Murine macrophages RAW 264.7 and J774A.1 cells were obtained from the American Type Culture Collection (Rockville, Md.). RAW 264.7 macrophages stably transfected with the NF-κB reporter gene (RAW-Blue™ cells) were purchased from InvivoGen (San Diego, Calif.). All cells were propagated in RPMI-1640 medium supplemented with 10% heat-inactivated fetal calf serum and 2 mM L-glutamine, and cultured at 37° C. in a 5% $CO_2$ incubator (RAW-Blue™ cells cultured in the presence of Zeocin™)

AlamarBlue® Assay for Cell Viability

Cells were seeded at a density of 5000 cells in 100 µl RPMI 1640 medium with 10% (v/v) fetal bovine serum per well in 96-well flat-bottom plates and incubated for 24 h at 37° C. in a 5% $CO_2$ incubator. Cells were incubated with tested samples for 24 h and the AlamarBlue® assay was used to determine the cytotoxicity of the test samples. The procedure was conducted following the protocol described in the manufacturer's instructions (AbD Serotec Ltd).

Enzyme-Linked Immunosorbent Assay (ELISA)

Cells were seeded in 6-well plates at a density of $5 \times 10^5$ cells/ml, and then incubated with or without LPS (1 µg/ml) in the absence or presence of tested samples for 24 h. The effects of tested samples on TNF-α, IL-6 and IL-1β production were measured by ELISA according to the manufacturer's protocol. In brief, 50 µl of biotinylated antibody reagent and 50 µl of supernatant were added to an anti-mouse TNF-α, IL-6 and IL-1β precoated stripwell plate, and incubated at room temperature for 2 h. After washing the plate three times with washing buffer, 100 µl of diluted streptavidin-HRP (horseradish peroxidase) concentrate was added to each well and incubated at room temperature for 30 min. The washing process was repeated; then 100 µl of a premixed tetramethylbenzidine substrate solution was added to each well and developed at room temperature in the dark for 30 min. Following the addition of 100 µl of stop solution to each well to stop the reaction, the absorbance of the plate was measured by a microplate reader at a 450 nm wavelength.

NO Inhibitory Assay

RAW 264.7 cells were seeded in 24-well plates at a density of $5 \times 10^5$ cells/ml, and then incubated with or without LPS (1 µg/ml) in the absence or presence of tested samples for 24 h. The effects of osthole on NO production were measured indirectly by analysis of nitrite levels using the Griess reaction.

NF-κB Reporter Assay

RAW-Blue™ cells, RAW 264.7 macrophages which stably express a secreted embryonic alkaline phosphatase (SEAP) gene inducible by NF-κB, were seeded in 60 mm dishes at a density of $5 \times 10^5$ cells/ml, and grown overnight in a 5% $CO_2$ incubator at 37° C. After pretreatment with tested samples followed by LPS stimulation for 24 h, the medium was harvested. Medium samples (20 µl) were then mixed with QUANTI-Blue™ (InvivoGen) medium (200 µl) in 96-well plates at 37° C. for 15 min. The results of SEAP activity were assessed by measuring the optical density at 655 nm using an ELISA reader.

Western Blot Assay

Whole cell lysates were separated by SDS-PAGE and electrotransferred to a PVDF (polyvinylidene fluoride) membrane. The membranes were incubated in blocking solution—5% nonfat milk in phosphate buffered saline with 0.1% Tween 20—at room temperature for 1 h. Each membrane was incubated with specific primary antibody at room temperature for 2 h. After washing three times in PBS with 0.1% Tween 20, the membrane was incubated with an HRP-conjugated secondary antibody directed against the primary antibody. The membrane was developed by an enhanced chemiluminescence Western blot detection system.

Statistical Analysis

All values are given as mean±SE. Data analysis involved one-way ANOVA with a subsequent Scheffe test.

Results

Characteristics of Bamboo Vinegar

Figure 1:
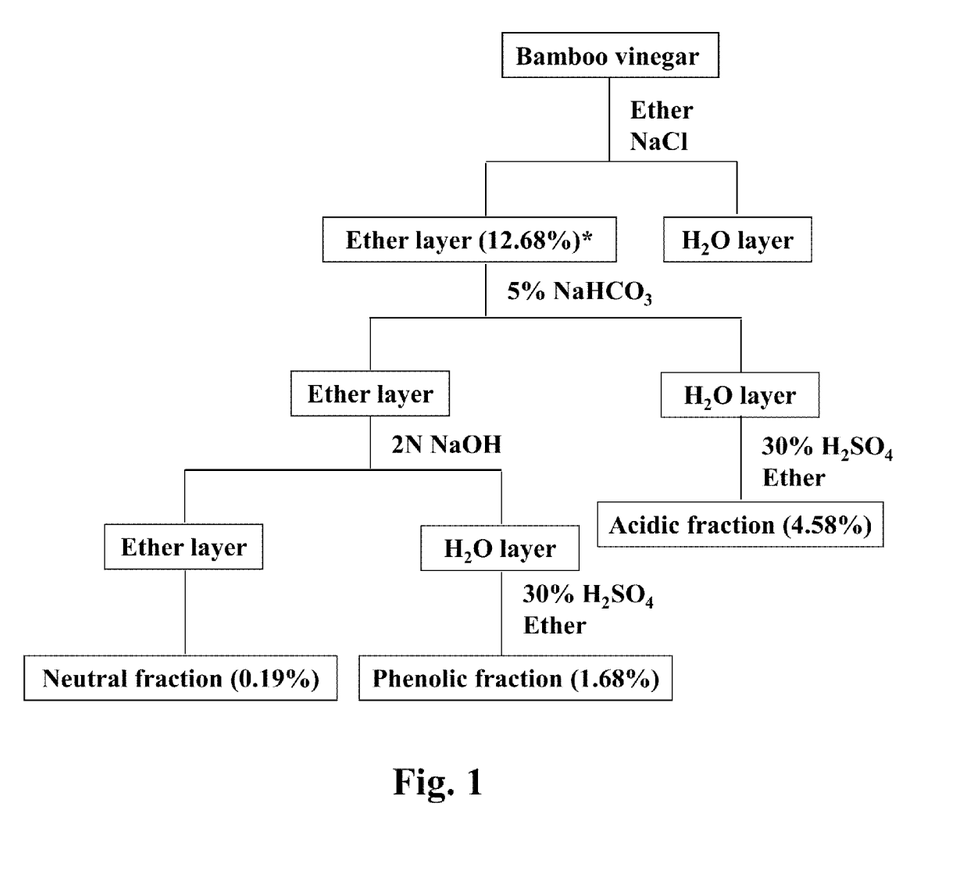
FIG. 1 shows the fractionation of moso bamboo vinegar from BV-4.

As shown in FIG. 1, there was 12.68% of the ether-extracted product for BV-4. Of the BV-4, the acidic fraction was the main fraction (4.58%) followed by the phenolic fraction (1.68%) and the neutral fraction (0.19%).

Bamboo vinegar reduced NO and IL-6 expression in LPS-activated macrophages

Figure 2A:
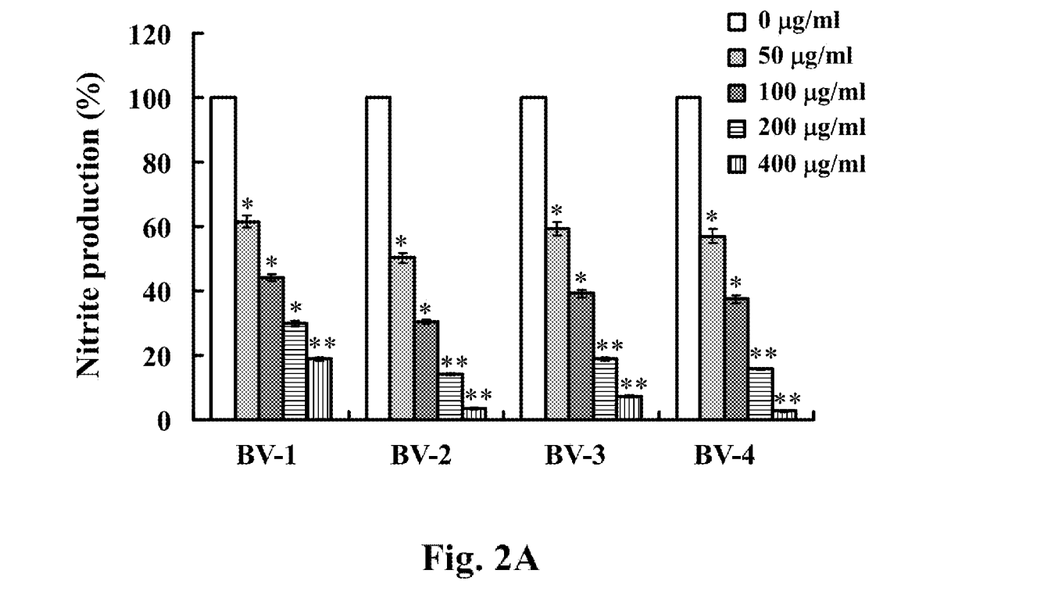
FIGS. 2A to 2D show the effects of BV-4 on the expression of inflammatory mediators; NO (A), IL-6 (B), TNF-α (C), iNOS and COX-2 (D) (*$p<0.05$; **$p<0.01$).

The effects of BV-4 on the expression of inflammatory mediators were evaluated. In this study, RAW 264.7 macrophages ($5 \times 10^5$/ml) were pretreated with BV-1~BV-4 for 30 min, followed by stimulating with LPS (1 µg/ml) for 24 h. NO concentration in culture medium was assayed by Griess reaction, wherein data were expressed as % of LPS alone ±SE from three separate experiments (*$p<0.05$; **$p<0.01$) as shown in FIG. 2A.

Figure 2B:
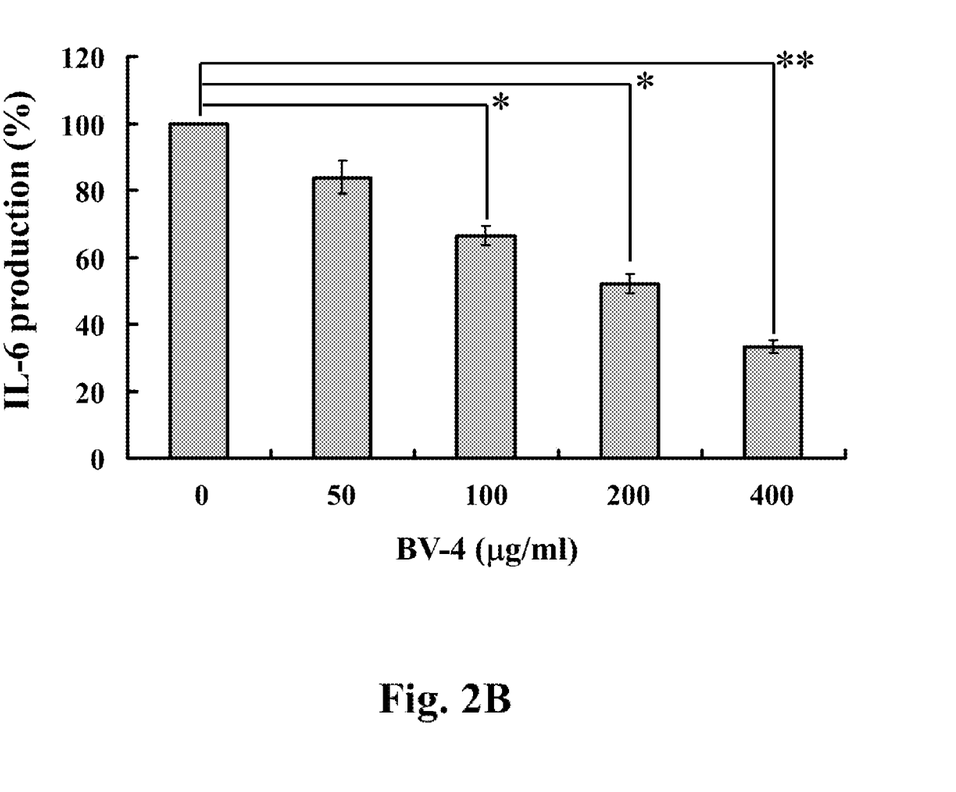
Figure 2C:
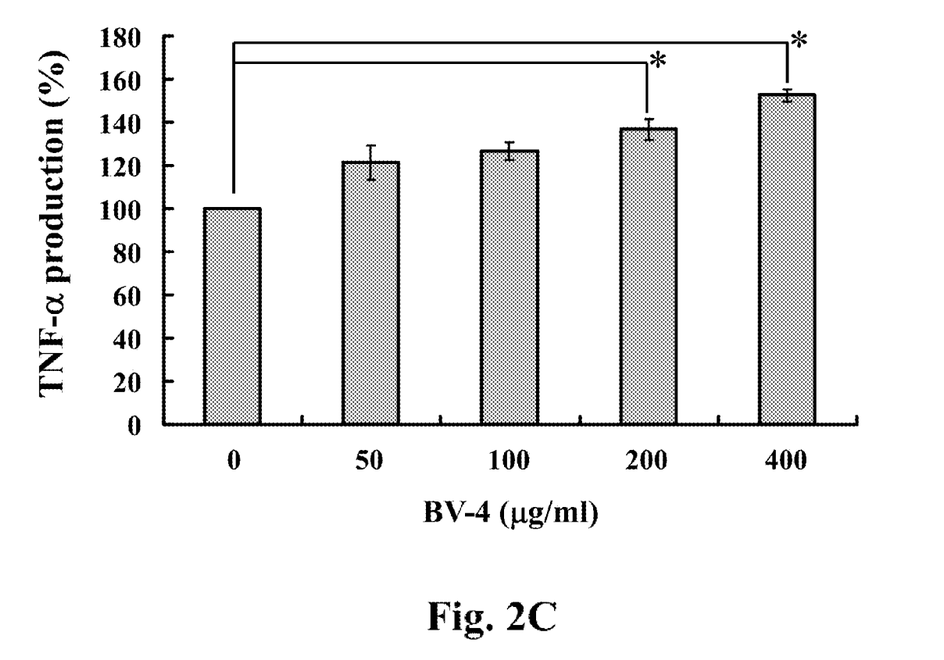

As shown in FIGS. 2B and 2C, RAW 264.7 macrophages ($5 \times 10^5$/ml) were pretreated with BV-4 for 30 min, followed by stimulating with LPS (1 µg/ml) for 24 h. IL-6 and TNF-α concentrations in culture medium were assayed by ELISA, wherein data were expressed as % of LPS alone ±SE from three separate experiments (*$p<0.05$; **$p<0.01$).

RAW 264.7 macrophages ($5 \times 10^5$/ml) were pretreated with BV-4 for 30 min, followed by stimulating with LPS (1 µg/ml) for 24 h. The expression of iNOS and COX-2 were assayed by Western blot. The result of one of three separate experiments was shown in FIG. 2D.

Figure 2D:
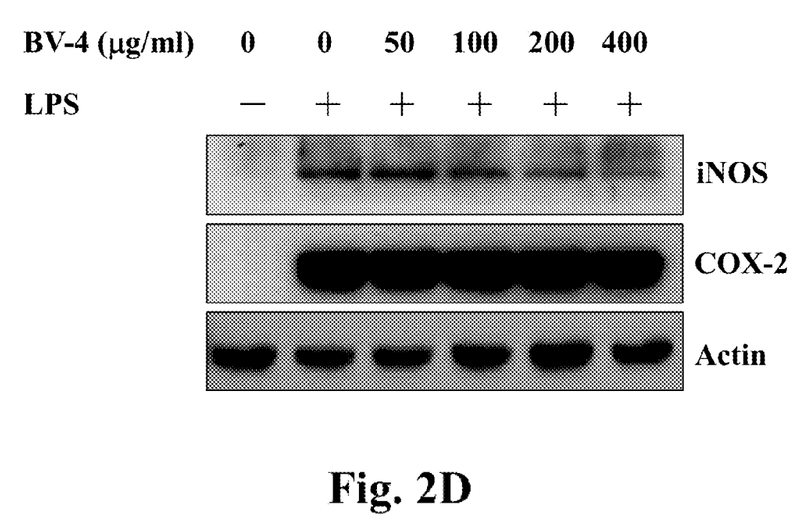
Figure 2E:
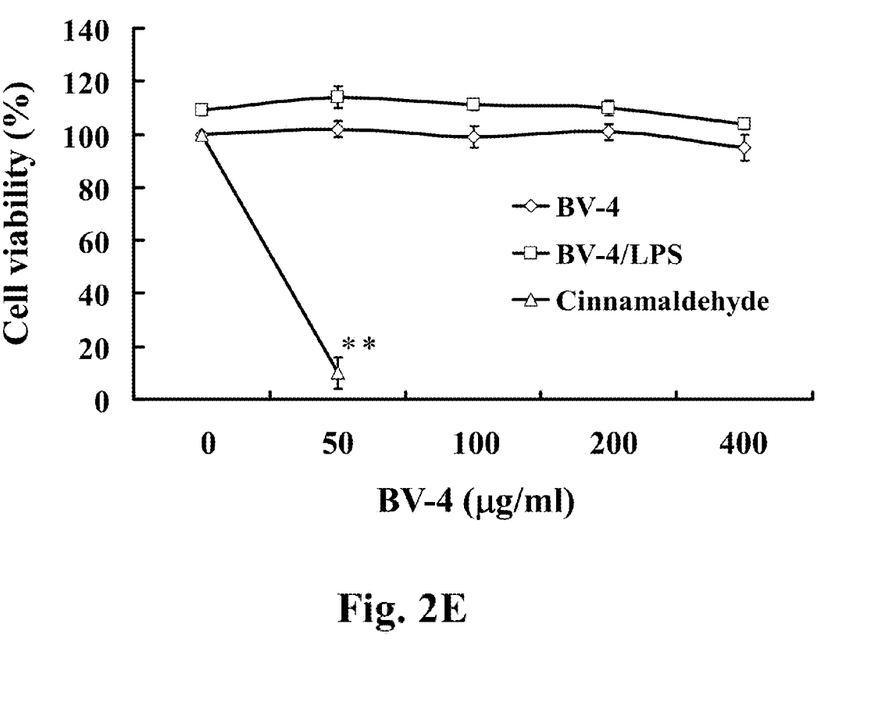
FIG. 2E shows the effect of BV-4 on cell viability.

The effects of BV-4 on cell viability were shown in FIG. 2E. The cells were treated with BV-4 or cinnamaldehyde (50 µM) in the presence or absence of LPS for 24 h, followed by incubating with MTT reagent. The absorbance (A550-A690) was measured by spectrophotometry. Data was expressed as means±SE, with three separate experiments (**$p<0.01$).

NO, IL-6, and TNF-α are important pro-inflammatory mediators produced mainly by activated macrophages and mediate multiple biological effects, including activation of immune responses. As shown in FIG. 2A, bamboo vinegar samples produced by different temperatures (BV-1: 90-92° C.; BV-2: 99-102° C.; BV-3: 120-123° C.; BV-4: 145-150° C.) have different effects on the NO expression in LPS-activated macrophages. In the study, Griess reaction was used to characterize the NO expression dose-response in BV-pretreated cells, and it was found that the NO expression was inhibited in all BV-pretreated cells in dose-dependent manner. Since the bamboo vinegar produced by different temperatures showed similar effect on LPS-induced NO expression, BV-4 was used for test in the following experiments. As shown in FIG. 2B, the BV-4 could affect cytokine expression in LPS-activated macrophages, an ELISA was used to characterize the cytokine expression dose-response in BV-4-pretreated cells and it was found that the expression of IL-6 was inhibited in dose-dependent manner. However, as shown in FIG. 2C, an increase of TNF-α expression in LPS-activated macrophages was found in the group of BV-4-pretreatment. As shown in FIG. 2D, the effect of BV-4 on the protein expression of inducible NO synthase (iNOS) and cyclooxygenase-2 (COX-2) was investigated and it was found that BV-4 bamboo vinegar reduced the expression of iNOS, but not COX-2 protein as compared with LPS treatment alone. To examine whether the reduction of NO and IL-6 expression were due to reduction of cell viability by BV-4 treatment, the toxicity of BV-4 was examined. Macrophages were treated with BV-4 at various concentrations (0, 50, 100, 200 and 400 µg/ml) in the absence or presence of LPS (1 µg/ml) for 24 h. Cell viability was analyzed by MTT assay. As shown in FIG. 2E, the results revealed that the cell survival rate did not differ significantly when macrophages were treated with <400 µg/ml BV-4. At these BV-4 concentrations, even the presence of LPS at 1 µg/ml did not affect the cell survival rate. Cinnamaldehyde was used as a positive control for reducing cell viability. In addition, BV-4 was found to be not toxic to another murine macrophage cell line, J774A.1, at concentrations ≦400 µg/ml (data not shown).

Figure 3A:
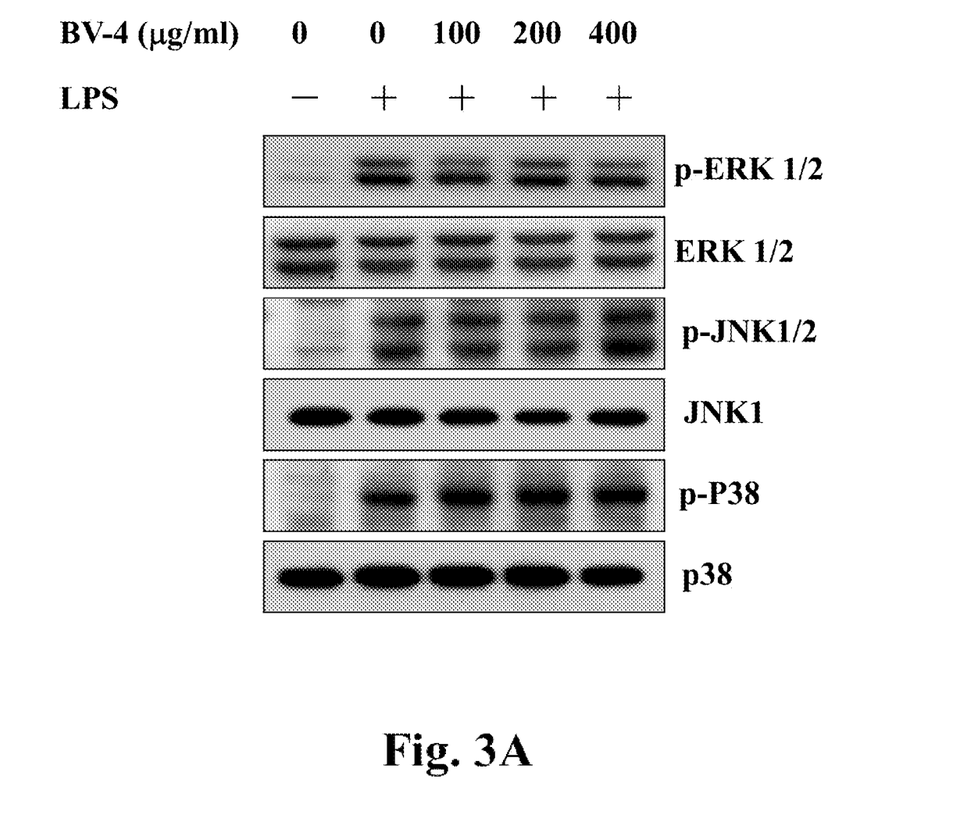
FIGS. 3A and 3B show the effects of BV-4 on MAPK phosphorylation, including ERK1/2, JNK-1/2, p38 (A), and AKT (B).
Figure 3B:
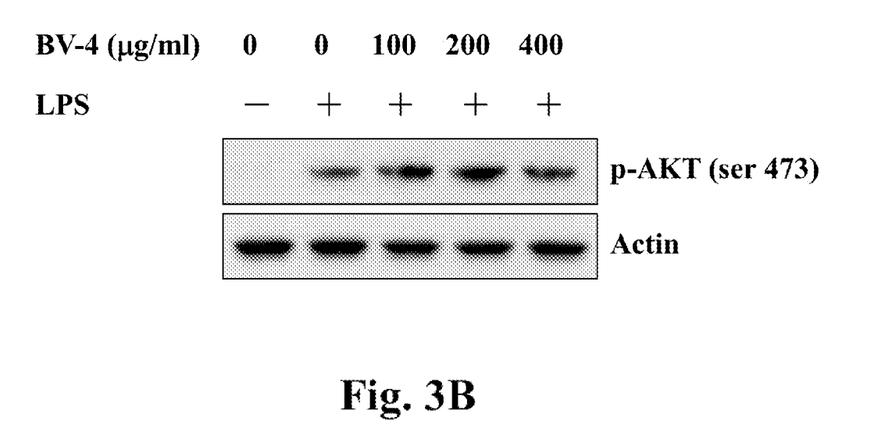
Figure 3C:
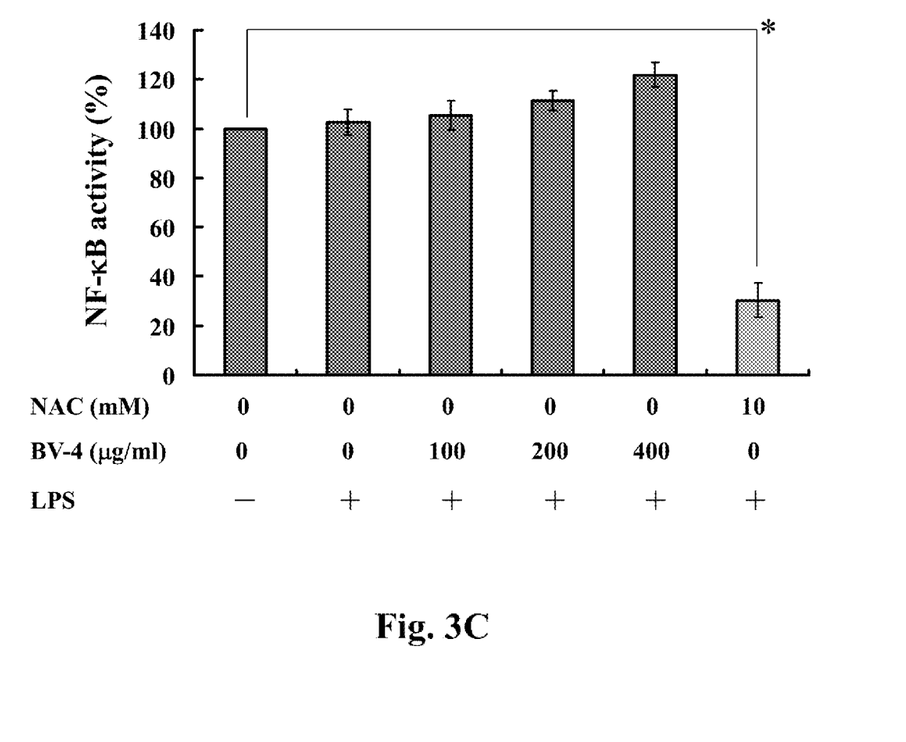
FIG. 3C shows the effect of BV-4 on NF-κB activation (*$p<0.05$).

BV-4 did not affect MAPK, AKT, and NF-κB signaling pathways in LPS-activated macrophages FIG. 3A to 3C show the effect of BV-4 on MAPK phosphorylation and NF-κB activation. RAW 264.7 macrophages ($5 \times 10^5$/ml) were pretreated with BV-4 for 30 min, followed by stimulating with LPS (1 µg/ml) for 20 min. (A) Phosphorylation levels of ERK1/2, JNK1/2, p38 and (B) AKT were analyzed by Western blot. The result of one of three separate experiments is shown. (C) RAW—Blue™ cells ($5 \times 10^6$/ml) were pretreated with BV-4 or NAC (10 mM) for 30 min, followed by stimulating with LPS (1 µg/ml) for 24 h. SEAP activity was measured by QUANTI-Blue™, wherein data are expressed as mean±SE from three separate experiments ($*p<0.05$).

LPS potently induces macrophage activation and the production of pro-inflammatory cytokines by the activation of TLR4 through many signaling pathways, including the MAPK and NF-κB signaling pathways. To examine whether the effects of BV-4 on LPS-induced macrophages were associated with MAPK signaling cascades, macrophages were treated with LPS in the presence or absence of BV-4. The phosphorylation levels of MAPK, including ERK1/2, JNK1/2, and p38 were determined by Western blot analysis. As shown in FIG. 3A, the experimental results showed that BV-4 did not affect the phosphorylation levels of ERK1/2, JNK1/2, and p38 in LPS-activated macrophages, indicating that BV-4 did not modulate the activation of the MAPK signaling cascades in LPS-activated macrophages.

In addition, it was also tested that the effect of BV-4 on the phosphorylation of AKT, one of the signaling molecules activated by LPS, and it was found that BV-4 did not affect AKT phosphorylation in LPS-activated macrophages, as shown in FIG. 3B. As shown in FIG. 3C, NF-κB-dependent alkaline phosphatase reporter cells were used to demonstrate that NF-κB transcriptional activity in LPS-stimulated macrophages was not reduced by BV-4; in contrast, BV-4 increased NF-κB transcriptional activity. These results indicated that BV-4 could not inhibit the activation of the NF-κB signaling cascades in LPS-activated macrophages.

BV-4 Inhibited PKC Signaling Pathways in LPS-Activated Macrophages

Figure 4A:
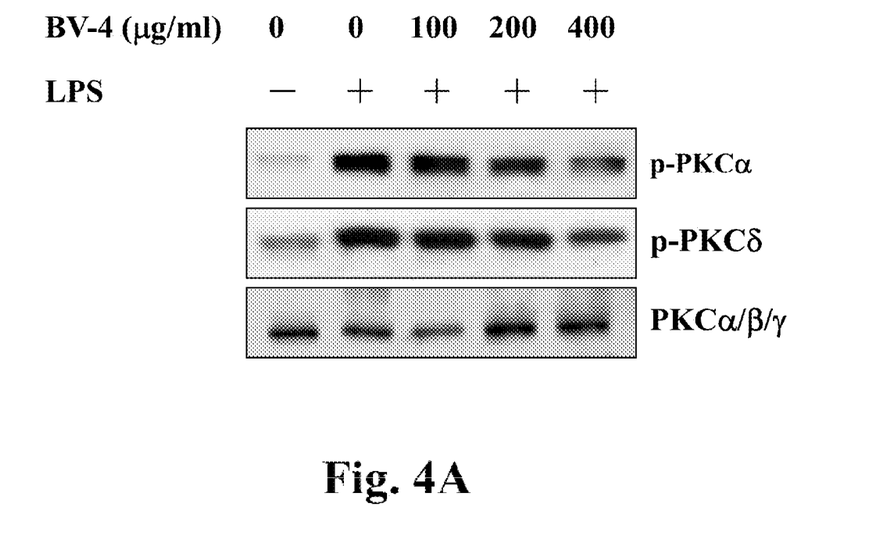
FIGS. 4A and 4B show the effects of BV-4 on PKC phosphorylation (*$p<0.05$).

The effects of BV-4 on PKC phosphorylation were also evaluated. RAW 264.7 macrophages ($5 \times 10^5$/ml) that were pretreated with BV-4 for 30 min, followed by stimulating with LPS (1 µg/ml) for 20 min. The result of one of the three separate experiments the phosphorylation levels of PKC-α and PKC-δ were analyzed by Western blot as shown in FIG. 4A; and the histogram representing the quantification by PhosphorImager of phosphor-PKC-α and phosphor-PKC-δ using ImageQuant software was shown in FIG. 4B ($*p<0.05$).

Figure 4B:
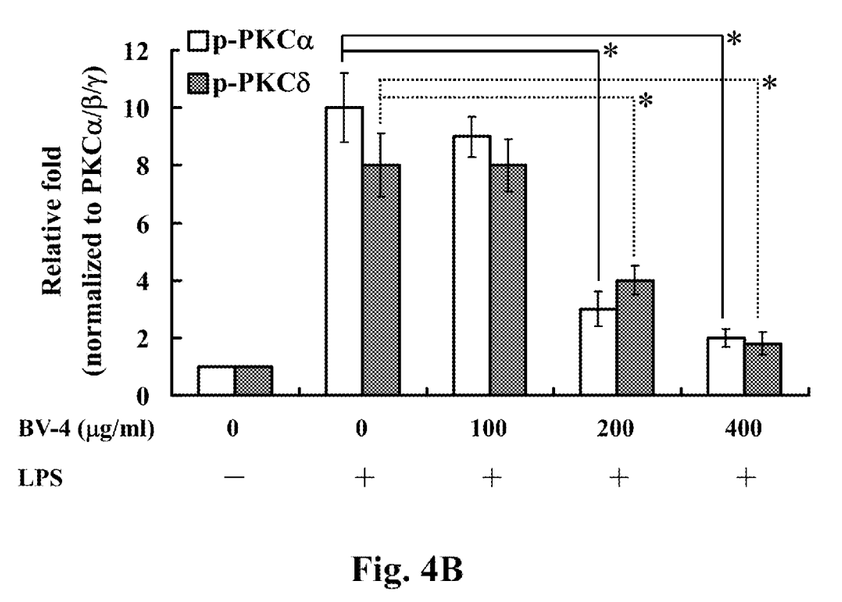

PKC is one of the components of the TLR4 signaling pathway, and thereby plays some roles in macrophage activation in response to LPS. To test the effect of BV-4 on LPS-induced PKC activation, the phosphorylation levels of PKC-α and PKC-δ were increased after LPS stimulation as shown in FIG. 4A. LPS-mediated phosphorylations of PKC-α and PKC-δ were reduced by BV-4 in dose-dependent manner. FIG. 4B showed the quantitative results of FIG. 4A.

Screening of the Bioactive Fraction of Bamboo Vinegar

Figure 5A:
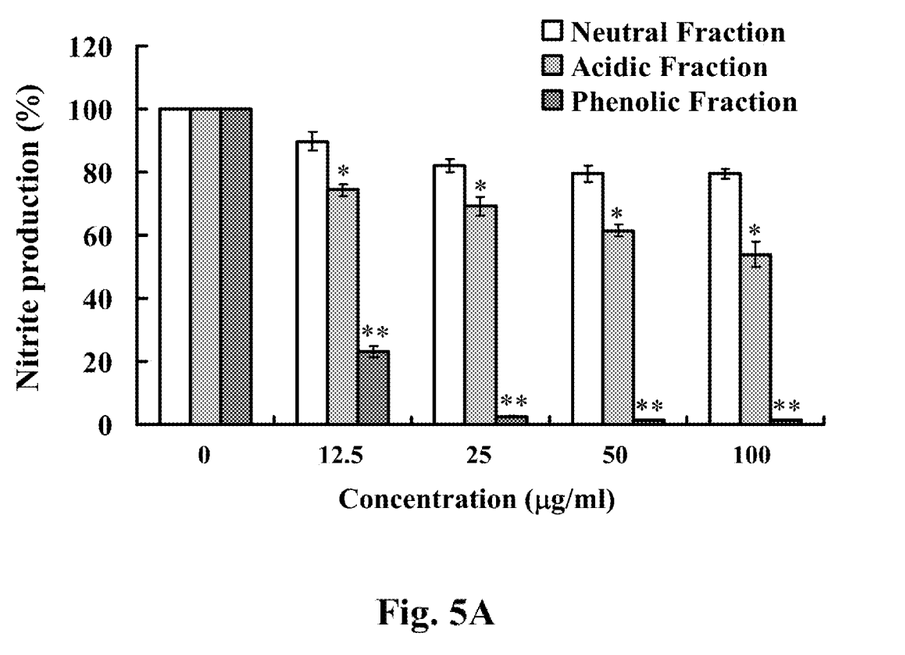
FIGS. 5A and 5B show the effects of fractionated BV-4 on NO expression (*$p<0.05$; **$p<0.01$).
Figure 5B:
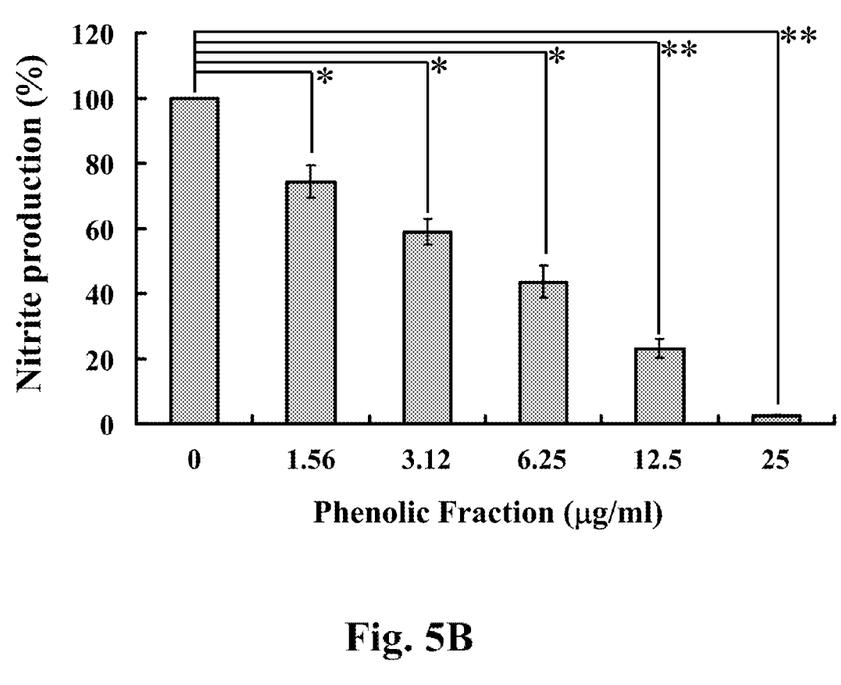

The effects of fractionated BV-4 on NO expression were evaluated as shown in FIGS. 5A and 5B. RAW 264.7 macrophages ($5 \times 10^5$/ml) were pretreated with acidic, neutral, and phenolic fractions of BV-4 (FIG. 5A) and the phenolic fraction of BV-4 (FIG. 5B) for 30 min, followed by stimulating with LPS (1 µg/ml) for 24 h. NO concentration in culture medium was assayed by Griess reaction, wherein data were expressed as % of LPS alone ±SE from three separate experiments ($*p<0.05$; $**p<0.01$) as shown in FIG. 5B. The cells were treated with the phenolic fraction of BV-4 in the presence or absence of LPS for 24 h, followed by incubating with MTT reagent. The absorbance (A550-A690) was measured by spectrophotometry, wherein data was expressed as means±SE, with three separate experiments ($*p<0.05$), see FIG. 5C.

Figure 5C:
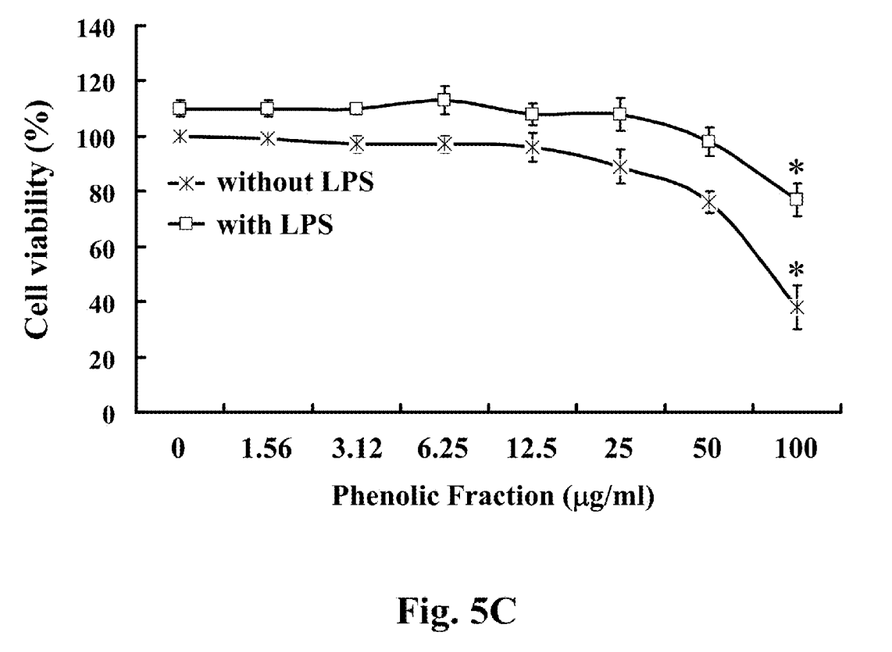
FIG. 5C shows the effect of the phenolic fraction of BV-4 on cell viability (*$p<0.05$).

To look for the anti-inflammatory ingredient of BV-4, the BV-4 was fractioned into neutral, acidic, and phenolic fractions and these fractions were evaluated for their anti-inflammatory activity. It was found that the phenolic fraction, but not the neutral fraction and the acidic fraction significantly inhibited NO expression in LPS-activated macrophages in dose-dependent manner (FIGS. 5A and 5B). The effect of the phenolic fraction of BV-4 on cell viability was also tested and it was found that the cell viability was not reduced significantly by the phenolic fraction 50 µg/ml (FIG. 5C).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

We claim:

1. A method of treating an inflammatory disorder in a human in need thereof comprising administering to the human a therapeutically effective amount of bamboo vinegar, wherein the bamboo vinegar is a phenolic fraction obtained from a method comprising the steps of:
   (a) distilling bamboo to obtain a distilled bamboo product, which is then extracted with diethyl ether to obtain an ethyl fraction;
   (b) extracting the ethyl fraction obtained in step (a) with a NaHCO$_3$ solution to collect a first organic layer;
   (c) extracting the first organic layer obtained in step (b) with a NaOH solution to collect an aqueous layer; and
   (d) extracting the aqueous layer obtained in step (c) with diethyl ether and an acidic solution selected from the group consisting of H$_2$SO$_4$ and HCl to obtain a second organic layer which contains the bamboo vinegar which is used to treat the inflammatory disorder in the human in need thereof.

2. The method of claim 1, wherein the NaHCO$_3$ solution has a pH value ranging from 7 to 8.

3. The method of claim 1, wherein the NaOH solution has a pH value ranging from 11 to 13.

4. The method of claim 1, wherein the acidic solution has a pH ranging from 2 to 4.

* * * * *